United States Patent
Auth et al.

(10) Patent No.: US 12,171,457 B2
(45) Date of Patent: Dec. 24, 2024

(54) ATHERECTOMY BURRS WITH BLOOD FLOW ENHANCEMENTS

(71) Applicant: BOSTON SCIENTIFIC SCIMED, INC., Maple Grove, MN (US)

(72) Inventors: David C. Auth, Hobe Sound, FL (US); Aparna Bhave, Woodbury, MN (US); Gary Thomas Ohrt, Corcoran, MN (US); Travis J. Schauer, Rockford, MN (US); Neha Sharma, Crystal, MN (US); Evan Bennett, Minneapolis, MN (US); Andrew Bicek, Elk River, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 130 days.

(21) Appl. No.: 17/514,368

(22) Filed: Oct. 29, 2021

(65) Prior Publication Data
US 2022/0133347 A1    May 5, 2022

Related U.S. Application Data

(60) Provisional application No. 63/108,045, filed on Oct. 30, 2020.

(51) Int. Cl.
*A61B 17/3207* (2006.01)
*A61B 17/32* (2006.01)

(52) U.S. Cl.
CPC .............. *A61B 17/320758* (2013.01); *A61B 2017/320004* (2013.01)

(58) Field of Classification Search
CPC ........ A61B 17/320758; A61B 17/3207; A61B 2017/320004; A61B 2017/32004; A61B 17/320725; A61B 2017/320766; A61B 17/32002; A61B 17/320783; A61B 2017/22094; A61B 17/1615
See application file for complete search history.

(56) References Cited

U.S. PATENT DOCUMENTS 2,088,654 A    8/1937    Hull
3,913,196 A    10/1975   Maday
(Continued)

FOREIGN PATENT DOCUMENTS

CA    2682488 A1    10/2008
DE    202005022017 U1    5/2012
(Continued)

OTHER PUBLICATIONS

International Search Report and Written Opinion dated Feb. 22, 2022 for International Application No. PCT/US2021/057279.
(Continued)

*Primary Examiner* — Mohamed G Gabr
*Assistant Examiner* — Aman Kumar Mann
(74) *Attorney, Agent, or Firm* — Seager, Tufte & Wickhem, LLP

(57) ABSTRACT

An atherectomy system includes an atherectomy burr having one or more blood flow enhancement features that permit an increased level of blood flow past the burr relative to a blood flow that would result absent the one or more flow enhancement features. A drive mechanism is adapted to rotatably actuate the atherectomy burr.

6 Claims, 11 Drawing Sheets

(56) References Cited

U.S. PATENT DOCUMENTS

| | | | |
|---|---|---|---|
| 3,937,222 A * | 2/1976 | Banko | A61F 9/00763 606/107 |
| 4,395,167 A | 7/1983 | Maternus | |
| 4,507,028 A | 3/1985 | Matsushita | |
| 4,679,557 A | 7/1987 | Opie et al. | |
| 4,990,134 A * | 2/1991 | Auth | A61B 17/320758 604/22 |
| 5,116,350 A | 5/1992 | Stevens | |
| 5,287,858 A | 2/1994 | Hammerslag et al. | |
| 5,308,354 A | 5/1994 | Zacca et al. | |
| 5,314,407 A | 5/1994 | Auth et al. | |
| 5,417,703 A | 5/1995 | Brown et al. | |
| 5,478,344 A | 12/1995 | Stone et al. | |
| 5,501,694 A | 3/1996 | Ressemann et al. | |
| 5,540,707 A | 7/1996 | Ressemann et al. | |
| 5,563,481 A | 10/1996 | Krause | |
| 5,572,609 A | 11/1996 | Li | |
| 5,626,444 A | 5/1997 | Campian | |
| 5,632,755 A * | 5/1997 | Nordgren | A61B 17/32075 606/159 |
| 5,674,235 A | 10/1997 | Parisi | |
| 5,681,336 A | 10/1997 | Clement et al. | |
| 5,709,661 A | 1/1998 | Van Egmond et al. | |
| 5,766,192 A | 6/1998 | Zacca | |
| 5,779,722 A | 7/1998 | Shturman et al. | |
| 5,823,990 A | 10/1998 | Henley | |
| 5,827,323 A | 10/1998 | Klieman et al. | |
| 5,836,868 A | 11/1998 | Ressemann et al. | |
| 5,899,915 A | 5/1999 | Saadat | |
| 5,913,867 A | 6/1999 | Dion | |
| 6,015,420 A | 1/2000 | Wulfman et al. | |
| 6,017,354 A | 1/2000 | Culp et al. | |
| 6,086,608 A | 7/2000 | Ek et al. | |
| 6,102,926 A | 8/2000 | Tartaglia et al. | |
| 6,106,301 A | 8/2000 | Merril | |
| 6,113,615 A | 9/2000 | Wulfman | |
| 6,120,515 A | 9/2000 | Rogers et al. | |
| 6,126,667 A | 10/2000 | Barry et al. | |
| 6,139,510 A | 10/2000 | Palermo | |
| 6,149,663 A | 11/2000 | Strandberg et al. | |
| 6,171,312 B1 | 1/2001 | Beaty | |
| 6,200,329 B1 | 3/2001 | Fung et al. | |
| 6,212,300 B1 | 4/2001 | Rengakuji | |
| 6,234,725 B1 | 5/2001 | Campian | |
| 6,270,509 B1 * | 8/2001 | Barry | A61B 17/320758 606/159 |
| 6,312,438 B1 | 11/2001 | Adams | |
| 6,494,888 B1 | 12/2002 | Laufer et al. | |
| 6,500,186 B2 | 12/2002 | Lafontaine et al. | |
| 6,503,227 B1 | 1/2003 | Guo et al. | |
| 6,503,261 B1 | 1/2003 | Bruneau et al. | |
| 6,506,196 B1 | 1/2003 | Laufer | |
| 6,554,845 B1 | 4/2003 | Fleenor et al. | |
| 6,569,085 B2 | 5/2003 | Kortenbach et al. | |
| 6,572,630 B1 * | 6/2003 | McGuckin, Jr. | A61B 17/320758 606/159 |
| 6,579,298 B1 * | 6/2003 | Bruneau | A61B 17/320758 606/159 |
| 6,626,917 B1 | 9/2003 | Craig | |
| 6,632,230 B2 | 10/2003 | Barry | |
| 6,663,639 B1 | 12/2003 | Laufer et al. | |
| 6,719,763 B2 | 4/2004 | Chung et al. | |
| 6,740,030 B2 | 5/2004 | Martone et al. | |
| 6,746,457 B2 | 6/2004 | Dana et al. | |
| 6,755,843 B2 | 6/2004 | Chung et al. | |
| 6,773,441 B1 | 8/2004 | Laufer et al. | |
| 6,808,491 B2 | 10/2004 | Kortenbach et al. | |
| 6,818,001 B2 | 11/2004 | Wulfman et al. | |
| 6,821,285 B2 | 11/2004 | Laufer et al. | |
| 6,835,200 B2 | 12/2004 | Laufer et al. | |
| 6,908,427 B2 | 6/2005 | Fleener et al. | |
| 6,997,931 B2 | 2/2006 | Sauer et al. | |
| 7,056,284 B2 | 6/2006 | Martone et al. | |
| 7,063,710 B2 | 6/2006 | Takamoto et al. | |
| 7,063,715 B2 | 6/2006 | Onuki et al. | |
| 7,094,246 B2 | 8/2006 | Anderson et al. | |
| 7,144,401 B2 | 12/2006 | Yamamoto et al. | |
| 7,147,646 B2 | 12/2006 | Dana et al. | |
| 7,153,314 B2 | 12/2006 | Laufer et al. | |
| 7,220,266 B2 | 5/2007 | Gambale | |
| 7,232,445 B2 | 6/2007 | Kortenbach et al. | |
| 7,235,086 B2 | 6/2007 | Sauer et al. | |
| 7,285,130 B2 | 10/2007 | Austin | |
| 7,326,221 B2 | 2/2008 | Sakamoto et al. | |
| 7,344,545 B2 | 3/2008 | Takemoto et al. | |
| 7,347,863 B2 | 3/2008 | Rothe et al. | |
| 7,361,180 B2 | 4/2008 | Saadat et al. | |
| 7,530,985 B2 | 5/2009 | Takemoto et al. | |
| 7,601,161 B1 | 10/2009 | Nobles et al. | |
| 7,618,425 B2 | 11/2009 | Yamamoto et al. | |
| 7,713,277 B2 | 5/2010 | Laufer et al. | |
| 7,722,633 B2 | 5/2010 | Laufer et al. | |
| 7,727,246 B2 | 6/2010 | Sixto, Jr. et al. | |
| 7,736,373 B2 | 6/2010 | Laufer et al. | |
| 7,776,057 B2 | 8/2010 | Laufer et al. | |
| 7,776,066 B2 | 8/2010 | Onuki et al. | |
| 7,842,051 B2 | 11/2010 | Dana et al. | |
| 7,846,180 B2 | 12/2010 | Cerier | |
| 7,857,823 B2 | 12/2010 | Laufer et al. | |
| 7,896,893 B2 | 3/2011 | Laufer et al. | |
| 7,918,867 B2 | 4/2011 | Dana et al. | |
| 7,951,157 B2 | 5/2011 | Gambale | |
| 7,992,571 B2 | 8/2011 | Gross et al. | |
| 7,993,368 B2 | 8/2011 | Gambale et al. | |
| 8,016,840 B2 | 9/2011 | Takemoto et al. | |
| 8,021,376 B2 | 9/2011 | Takemoto et al. | |
| 8,057,494 B2 | 11/2011 | Laufer et al. | |
| 8,062,314 B2 | 11/2011 | Sixto, Jr. et al. | |
| 8,066,721 B2 | 11/2011 | Kortenbach et al. | |
| 8,087,856 B2 | 1/2012 | Reed | |
| 8,105,355 B2 | 1/2012 | Page et al. | |
| 8,211,123 B2 | 7/2012 | Gross et al. | |
| 8,216,253 B2 | 7/2012 | Saadat et al. | |
| 8,226,667 B2 | 7/2012 | Viola et al. | |
| 8,277,468 B2 | 10/2012 | Laufer et al. | |
| 8,287,554 B2 | 10/2012 | Cerier et al. | |
| 8,287,556 B2 | 10/2012 | Gilkey et al. | |
| 8,308,765 B2 | 11/2012 | Saadat et al. | |
| 8,313,496 B2 | 11/2012 | Sauer et al. | |
| 8,361,089 B2 | 1/2013 | Chu | |
| 8,388,632 B2 | 3/2013 | Gambale | |
| 8,425,555 B2 | 4/2013 | Page et al. | |
| 8,454,631 B2 | 6/2013 | Viola et al. | |
| 8,480,691 B2 | 7/2013 | Dana et al. | |
| 8,540,735 B2 | 9/2013 | Mitelberg et al. | |
| 8,551,120 B2 | 10/2013 | Gambale | |
| 8,556,914 B2 | 10/2013 | Vrba | |
| 8,585,720 B2 | 11/2013 | Gross et al. | |
| 8,603,123 B2 | 12/2013 | Todd | |
| 8,632,553 B2 | 1/2014 | Sakamoto et al. | |
| 8,679,136 B2 | 3/2014 | Mitelberg | |
| 8,702,735 B2 * | 4/2014 | Rivers | A61B 17/320758 606/159 |
| 8,709,022 B2 | 4/2014 | Stone et al. | |
| 8,764,771 B2 | 7/2014 | Chu | |
| 8,882,785 B2 | 11/2014 | Dicesare et al. | |
| 8,926,634 B2 | 1/2015 | Rothe et al. | |
| 8,992,570 B2 | 3/2015 | Gambale et al. | |
| 9,011,466 B2 | 4/2015 | Overes et al. | |
| 9,050,126 B2 | 6/2015 | Rivers et al. | |
| 9,050,127 B2 | 6/2015 | Bonnette et al. | |
| 9,089,325 B2 | 7/2015 | Mitelberg et al. | |
| 9,125,646 B2 | 9/2015 | Woodard, Jr. et al. | |
| 9,198,562 B2 | 12/2015 | Mitelberg et al. | |
| 9,232,957 B2 | 1/2016 | Adams | |
| 9,320,515 B2 | 4/2016 | Dana et al. | |
| 9,474,536 B2 | 10/2016 | Carrison et al. | |
| 9,486,126 B2 | 11/2016 | West et al. | |
| 9,504,465 B2 | 11/2016 | Chu | |
| 9,510,817 B2 | 12/2016 | Saadat et al. | |
| 9,549,728 B2 | 1/2017 | Chu | |
| 9,750,494 B2 | 9/2017 | Gross et al. | |

(56) References Cited

U.S. PATENT DOCUMENTS

| | | | |
|---|---|---|---|
| 9,788,831 B2 | 10/2017 | Mitelberg | |
| 9,844,366 B2 | 12/2017 | Woodard, Jr. et al. | |
| 9,867,610 B2 | 1/2018 | Mitelberg et al. | |
| 9,931,488 B2 | 4/2018 | Bunch et al. | |
| 10,045,871 B2 | 8/2018 | Saadat et al. | |
| 10,052,122 B2 | 8/2018 | Higgins et al. | |
| 10,130,437 B2 | 11/2018 | Lee et al. | |
| 10,143,463 B2 | 12/2018 | Dana et al. | |
| 10,194,902 B2 | 2/2019 | Nobles et al. | |
| 10,335,142 B2 | 7/2019 | Raybin et al. | |
| 10,736,628 B2 | 8/2020 | Yates et al. | |
| 11,259,835 B2 * | 3/2022 | Smith | A61B 17/320758 |
| 2001/0004700 A1 | 6/2001 | Honeycutt et al. | |
| 2001/0037121 A1 | 11/2001 | McGuckin, Jr. et al. | |
| 2002/0007190 A1 * | 1/2002 | Wulfman | A61B 17/320725 |
| | | | 606/171 |
| 2002/0058956 A1 | 5/2002 | Honeycutt et al. | |
| 2002/0107530 A1 | 8/2002 | Sauer et al. | |
| 2002/0151917 A1 | 10/2002 | Barry | |
| 2002/0161384 A1 | 10/2002 | Wulfman et al. | |
| 2003/0093103 A1 | 5/2003 | Malackowski et al. | |
| 2003/0204205 A1 | 10/2003 | Sauer et al. | |
| 2004/0002699 A1 | 1/2004 | Ryan et al. | |
| 2004/0068270 A1 | 4/2004 | Allred, III | |
| 2004/0138706 A1 | 7/2004 | Abrams et al. | |
| 2004/0186368 A1 | 9/2004 | Ramzipoor et al. | |
| 2005/0004579 A1 | 1/2005 | Schneider et al. | |
| 2005/0015021 A1 | 1/2005 | Shiber | |
| 2005/0033319 A1 | 2/2005 | Gambale et al. | |
| 2005/0240146 A1 | 10/2005 | Nash et al. | |
| 2005/0250985 A1 | 11/2005 | Saadat et al. | |
| 2006/0074405 A1 | 4/2006 | Malackowski et al. | |
| 2006/0074442 A1 | 4/2006 | Noriega et al. | |
| 2006/0142775 A1 | 6/2006 | Heneberry et al. | |
| 2007/0093841 A1 | 4/2007 | Hoogland | |
| 2007/0239140 A1 | 10/2007 | Chechelski et al. | |
| 2007/0270908 A1 | 11/2007 | Stokes et al. | |
| 2008/0039823 A1 | 2/2008 | Shimogami et al. | |
| 2008/0086148 A1 | 4/2008 | Baker et al. | |
| 2008/0097499 A1 | 4/2008 | Nash et al. | |
| 2008/0103516 A1 * | 5/2008 | Wulfman | A61B 17/3207 |
| | | | 606/180 |
| 2008/0146965 A1 | 6/2008 | Privitera et al. | |
| 2009/0024085 A1 | 1/2009 | To et al. | |
| 2009/0069829 A1 | 3/2009 | Shturman | |
| 2009/0124975 A1 | 5/2009 | Oliver et al. | |
| 2009/0177031 A1 | 7/2009 | Surti et al. | |
| 2009/0299392 A1 * | 12/2009 | Rivers | A61B 17/320758 |
| | | | 606/159 |
| 2010/0125276 A1 | 5/2010 | Palermo | |
| 2010/0137681 A1 | 6/2010 | Ewers et al. | |
| 2010/0198006 A1 | 8/2010 | Greenburg et al. | |
| 2010/0292720 A1 * | 11/2010 | Thatcher | A61B 17/320758 |
| | | | 606/159 |
| 2010/0312263 A1 | 12/2010 | Moberg et al. | |
| 2011/0077673 A1 | 3/2011 | Grubac et al. | |
| 2011/0213391 A1 | 9/2011 | Rivers et al. | |
| 2011/0251554 A1 | 10/2011 | Romoscanu | |
| 2011/0306995 A1 | 12/2011 | Moberg | |
| 2012/0046600 A1 * | 2/2012 | Kohler | A61B 17/320758 |
| | | | 604/22 |
| 2012/0053606 A1 | 3/2012 | Schmitz et al. | |
| 2012/0095461 A1 | 4/2012 | Herscher et al. | |
| 2012/0130410 A1 | 5/2012 | Tal et al. | |
| 2012/0136348 A1 | 5/2012 | Condie et al. | |
| 2012/0158023 A1 | 6/2012 | Mitelberg et al. | |
| 2012/0172963 A1 | 7/2012 | Ryan et al. | |
| 2012/0179167 A1 | 7/2012 | Wenderow et al. | |
| 2012/0185031 A1 | 7/2012 | Ryan et al. | |
| 2012/0209176 A1 | 8/2012 | Anderson | |
| 2012/0271327 A1 | 10/2012 | West et al. | |
| 2013/0006248 A1 | 1/2013 | Ellis | |
| 2013/0079763 A1 | 3/2013 | Heckel et al. | |
| 2013/0096581 A1 | 4/2013 | Gilkey et al. | |
| 2013/0103062 A1 | 4/2013 | To et al. | |
| 2013/0253552 A1 | 9/2013 | Schoenle et al. | |
| 2013/0274657 A1 | 10/2013 | Zirps et al. | |
| 2013/0304093 A1 | 11/2013 | Serina et al. | |
| 2014/0100574 A1 | 4/2014 | Bono et al. | |
| 2014/0128668 A1 | 5/2014 | Cox et al. | |
| 2014/0148835 A1 | 5/2014 | Schmitz et al. | |
| 2014/0212457 A1 | 7/2014 | Rifai | |
| 2014/0222042 A1 | 8/2014 | Kessler et al. | |
| 2014/0249554 A1 | 9/2014 | To et al. | |
| 2014/0261453 A1 | 9/2014 | Carlson | |
| 2014/0277014 A1 | 9/2014 | Higgins et al. | |
| 2014/0316447 A1 | 10/2014 | Ellering et al. | |
| 2014/0316448 A1 | 10/2014 | Higgins | |
| 2014/0316451 A1 | 10/2014 | Higgins et al. | |
| 2014/0324052 A1 | 10/2014 | Carrison et al. | |
| 2015/0011834 A1 | 1/2015 | Ayala et al. | |
| 2015/0073448 A1 | 3/2015 | Rydberg | |
| 2015/0125807 A1 | 5/2015 | Shipley | |
| 2015/0126983 A1 | 5/2015 | Alvarado et al. | |
| 2015/0164540 A1 | 6/2015 | Higgins et al. | |
| 2015/0173776 A1 | 6/2015 | Burke et al. | |
| 2015/0173838 A1 | 6/2015 | Murphy et al. | |
| 2015/0201956 A1 | 7/2015 | Higgins et al. | |
| 2015/0216554 A1 | 8/2015 | Kessler et al. | |
| 2015/0327880 A1 | 11/2015 | Wasicek et al. | |
| 2015/0335348 A1 | 11/2015 | Cohen et al. | |
| 2016/0022307 A1 | 1/2016 | Wasdyke et al. | |
| 2016/0045197 A1 | 2/2016 | Mitelberg et al. | |
| 2016/0157886 A1 | 6/2016 | WasDyke et al. | |
| 2016/0235434 A1 | 8/2016 | Smith et al. | |
| 2016/0235441 A1 | 8/2016 | Parkin | |
| 2016/0287284 A1 * | 10/2016 | Smith | A61B 17/320725 |
| 2016/0346003 A1 | 12/2016 | Grothe et al. | |
| 2016/0354107 A1 | 12/2016 | Nakano et al. | |
| 2017/0014146 A1 * | 1/2017 | Guggenheimer | A61B 17/320783 |
| 2017/0086817 A1 | 3/2017 | Mitelberg | |
| 2017/0086818 A1 | 3/2017 | Mitelberg | |
| 2017/0181760 A1 | 6/2017 | Look et al. | |
| 2017/0189123 A1 | 7/2017 | Govari et al. | |
| 2017/0273698 A1 | 9/2017 | McGuckin, Jr. et al. | |
| 2017/0296200 A1 | 10/2017 | Singer et al. | |
| 2018/0042602 A1 | 2/2018 | Mitelberg et al. | |
| 2018/0042603 A1 | 2/2018 | Mitelberg et al. | |
| 2018/0153381 A1 | 6/2018 | Wei et al. | |
| 2018/0183179 A1 | 6/2018 | Byrd et al. | |
| 2018/0193056 A1 * | 7/2018 | Colyer | A61B 17/3207 |
| 2018/0235604 A1 | 8/2018 | Comee et al. | |
| 2018/0242998 A1 | 8/2018 | Dhandhusaria et al. | |
| 2019/0175211 A1 | 6/2019 | Carlson et al. | |
| 2019/0262032 A1 | 8/2019 | Carlson et al. | |
| 2019/0262924 A1 | 8/2019 | Spangler et al. | |
| 2020/0022764 A1 | 1/2020 | Flexman et al. | |
| 2020/0060718 A1 | 2/2020 | Patel et al. | |
| 2020/0069324 A1 | 3/2020 | Deepa | |
| 2020/0229844 A1 | 7/2020 | Rawson et al. | |
| 2020/0315654 A1 | 10/2020 | Patel et al. | |
| 2021/0172499 A1 | 6/2021 | Nino | |

FOREIGN PATENT DOCUMENTS

| | | |
|---|---|---|
| EP | 1520509 A1 | 4/2005 |
| EP | 2011446 A2 | 7/2009 |
| EP | 2108304 A2 | 10/2009 |
| EP | 2508141 A1 | 10/2012 |
| EP | 3053534 A1 | 8/2016 |
| EP | 3132760 A1 | 2/2017 |
| EP | 3192461 A1 | 7/2017 |
| EP | 3222228 A1 | 9/2017 |
| EP | 3226784 B1 | 9/2020 |
| IE | S2009529 A2 | 4/2012 |
| JP | H10174689 A | 6/1998 |
| JP | 2001509685 A | 7/2001 |
| WO | 9629014 A1 | 9/1996 |
| WO | 9814124 A1 | 4/1998 |
| WO | 0051511 A1 | 9/2000 |
| WO | 0056230 A2 | 9/2000 |
| WO | 2001054595 A1 | 8/2001 |

(56) References Cited

FOREIGN PATENT DOCUMENTS

| | | | |
|---|---|---|---|
| WO | 0189393 | A1 | 11/2001 |
| WO | 0249518 | A2 | 6/2002 |
| WO | 2004080507 | A2 | 9/2004 |
| WO | 2008016592 | A2 | 2/2008 |
| WO | 2008045376 | A2 | 4/2008 |
| WO | 2008098124 | A1 | 8/2008 |
| WO | 2010036227 | A1 | 4/2010 |
| WO | 2010056714 | A1 | 5/2010 |
| WO | 2010089727 | A1 | 8/2010 |
| WO | 2011060192 | A1 | 5/2011 |
| WO | 2011106053 | A1 | 9/2011 |
| WO | 2013158849 | A2 | 10/2013 |
| WO | 2014106847 | A1 | 7/2014 |
| WO | 2016001932 | A1 | 1/2016 |
| WO | 2016144834 | A1 | 9/2016 |
| WO | 2016200811 | A1 | 12/2016 |
| WO | 2017087856 | A1 | 5/2017 |
| WO | 2018156603 | A1 | 8/2018 |
| WO | 2019118522 | A1 | 6/2019 |
| WO | 2019168784 | A1 | 9/2019 |
| WO | 2020055728 | A1 | 3/2020 |

OTHER PUBLICATIONS

International Search Report and Written Opinion dated Aug. 20, 2019 for International Application No. PCT/US2019/033748.
International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
Invitation to Pay Additional Fees dated Nov. 18, 2019 for International Application No. PCT/US2019/049774.
International Search and Written Opinion dated Sep. 20, 2019 for International Application No. PCT/2019/039312.
International Search Report and Written Opinion dated Jun. 4, 2021 for International Application No. PCT/US2021/017939.
International Search Report and Written opinion dated Mar. 28, 2018 for International Application No. PCT/US2018/013587.
International Search Report and Written Opinion dated Apr. 17, 2019 for International Application No. PCT/US2019/018121.
International Search Report and Written Opinion dated Apr. 26, 2019, for International Application No. PCT/US2019/019404.
"What is a PID Controller: Working & Its Applications, 2013, EL-PRO-CUS, URL:https://www.elprocus.com/the-working-of-a-pid-controller/" 17 pages, (Year:2013).
International Search Report and Written Opinion dated Apr. 26, 2019, for International Application No. PCT/US2019/019631.
International Search Report and Written Opinion dated Mar. 30, 2020 for International Application No. PCT/US2020/014062.
International Search Report and Written Opinion dated Jun. 25, 2020 for International Application No. PCT/US2020/012767.
International Search Report and Written Opinion dated Apr. 22, 2020 for International Application No. PCT/US2020/013764.
International Search Report and Written Opinion dated Jun. 24, 2020 for International Application No. PCT/US2020/027079.
International Search Report and Written Opinion dated Sep. 4, 2020 for International Application No. PCT/US2020/038132.
International Search Report and Written Opinion dated Sep. 7, 2020 for International Application No. PCT/US2020/038145.
International Search Report and Written Opinion dated Dec. 8, 2020 for International Application No. PCT/US2020/049999.
Invite to Pay Additional Fees dated Feb. 16, 2021 for International Application No. PCT/US2020/061383.
International Search Report and Written Opinion dated Jan. 26, 2022 for International Application No. PCT/US2021/056616.
U.S. Appl. No. 17,706,866, filed Mar. 29, 2022.

\* cited by examiner

ATHERECTOMY BURRS WITH BLOOD FLOW ENHANCEMENTS

RELATED APPLICATIONS

This application claims the benefit under 35 USC 119 to U.S. Provisional Ser. No. 63/108,045, filed Oct. 30, 2020, which application is incorporated by reference herein.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, an atherectomy system includes an atherectomy burr having one or more blood flow enhancement features that permit an increased level of blood flow past the burr relative to a blood flow that would result absent the one or more flow enhancement features. The atherectomy burr includes a burr body and an outer surface as well as a drive mechanism that is adapted to rotatably actuate the atherectomy burr.

Alternatively or additionally, the drive mechanism may include a drive cable that is adapted to be coupled with the atherectomy burr and a prime mover that is adapted to rotate the drive cable.

Alternatively or additionally, an outer surface of the atherectomy burr may include an abrasive material.

Alternatively or additionally, substantially all of the plaque that is removed during operation of the atherectomy system may be removed by the abrasive material.

Alternatively or additionally, the one or more blood flow enhancement features may include blood flow grooves formed within the outer surface of the atherectomy burr.

Alternatively or additionally, the blood flow grooves may have a rounded over edge having a radius of curvatures sufficient to not provide a cutting edge.

Alternatively or additionally, the radius of curvature may be at least 0.0001 inches.

Alternatively or additionally, the one or more blood flow enhancement features may include a single asymmetric cut within the burr body.

Alternatively or additionally, the blood flow grooves may include a plurality of symmetrically arranged blood flow grooves extending axially along a length of the burr body.

Alternatively or additionally, the blood flow grooves may include one or more blood flow grooves extending spirally along a length of the burr body.

Alternatively or additionally, the one or more blood flow enhancement features may include one or more blood flow channels that pass through an interior of the burr body.

Alternatively or additionally, at least one of the one or more blood flow channels may extend axially through the interior of the burr body.

Alternatively or additionally, at least one of the one or more blood flow channels may extend radially into the interior of the burr body.

As another example, an atherectomy burr may be adapted for use in a rotational atherectomy system. The atherectomy burr includes an atherectomy burr body extending from a distal region to a proximal region thereof and adapted to be secured relative to a drive cable of a rotational atherectomy system. The atherectomy burr body defines an outer surface and includes one or more blood flow enhancement features that are adapted to increase blood flow past the burr.

Alternatively or additionally, the one or more blood flow enhancement features may include blood flow grooves formed within the outer surface of the atherectomy burr.

Alternatively or additionally, the one or more blood flow enhancement features may include a single asymmetric cut within the burr body.

Alternatively or additionally, the one or more blood flow enhancement features may include a plurality of symmetrically arranged blood flow grooves extending axially along a length of the burr body.

Alternatively or additionally, the one or more blood flow enhancement features may include one or more blood flow grooves extending spirally along a length of the burr body.

Alternatively or additionally, the one or more blood flow enhancement features may include one or more blood flow channels that pass through an interior of the burr body.

Alternatively or additionally, the one or more blood flow enhancement features may include two or more blood flow channels that are asymmetrically arranged about the outer surface of the atherectomy burr.

Alternatively or additionally, the one or more flow enhancement features may be adapted to provide preferential cutting of inelastic material relative to elastic material.

Alternatively or additionally, the one or more blood flow enhancement features may include a flow channel formed within the outer surface of the atherectomy burr, where the flow channel includes a chamfered leading edge.

Alternatively or additionally, the flow channel may include a semi-spiral channel.

Alternatively or additionally, the flow channel may include a straight flow channel arranged at an angle with respect to a longitudinal axis of the atherectomy burr.

As another example, an atherectomy burr may be adapted for use in a rotational atherectomy system. The atherectomy burr includes an atherectomy burr body extending from a distal region to a proximal region thereof and adapted to be secured relative to a drive cable of a rotational atherectomy system. The atherectomy burr body defines an outer surface, with a first blood flow enhancing groove formed in the outer surface and extending at least a portion of a length of the burr body and a second blood flow enhancing groove formed in the outer surface and extending at least a portion of the length of the burr body, the second blood flow enhancing groove spaced about 180 degrees circumferentially from the first blood flow enhancing groove.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
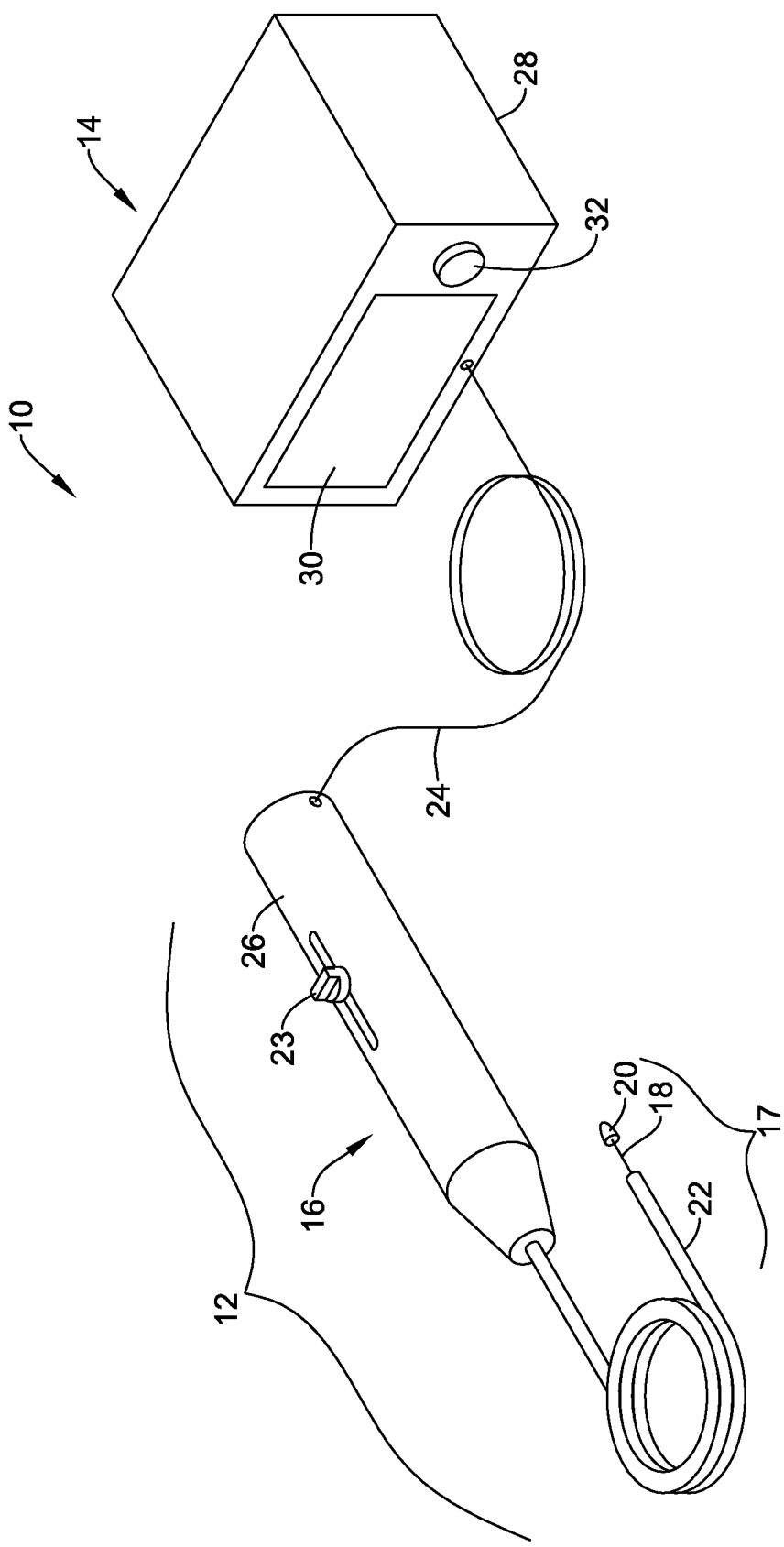
FIG. 1 is a schematic block diagram of an illustrative atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft or fatty, fibrous, or calcified. All are inelastic. The deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material (e.g., blocked by an occlusion). In an atherectomy procedure, a device on an end of a drive shaft is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction.

FIG. 1 depicts an atherectomy system 10. The atherectomy system 10 may be electrically driven, pneumatically driven and/or driven in one or more other suitable manner. Additional or alternative components to those illustrated and described herein may be utilized in the operation of the atherectomy system 10.

The atherectomy system 10 may include a drive assembly 12 and a control unit 14 (e.g., a controller). The drive assembly 12 may include, among other elements, an advancer assembly 16 and a rotation assembly 17. Although the control unit 14 is depicted as being separate from the drive assembly 12 in FIG. 1, the functionality of the control unit 14 and the drive assembly 12 may be incorporated into a single component (e.g., in the advancer assembly 16 or other suitable single component).

The rotation assembly 17 may include a drive shaft 18 (e.g., an elongate member that may be or may include a flexible drive shaft or other suitable drive shaft), an atherectomy burr 20, and an elongate member 22 having a first end (e.g., a proximal end), a second end (e.g., a distal end), and a lumen extending from the first end to the second end for receiving the drive shaft 18. In some cases, the elongate member 22 may be an elongated tubular member. The atherectomy burr 20 may have a rough surface, such that it is configured to grind, abrade, etc. plaque from a vessel wall or other obstruction in a vessel when it is rotated.

The advancer assembly 16 may include a knob 23, a housing 26, a drive mechanism (internal to the advancer assembly and thus not visible), and/or one or more other suitable components. The housing 26 may at least partially house the drive mechanism and the knob 23 may be at least partially accessible from an exterior of the housing 26. The drive mechanism may be or may include a motor (e.g., an electric motor, pneumatic motor, or other suitable motor) at least partially housed within the housing 26 and in communication with the knob 23, the drive shaft 18, and the control unit 14. The knob 23 may be configured to advance along a longitudinal path to longitudinally advance the drive mechanism and the rotation assembly 17.

The drive mechanism may be coupled to the drive shaft 18 in a suitable manner including, but not limited to, a weld connection, a clamping connection, an adhesive connection, a threaded connection, and/or other suitable connection configured to withstand rotational speeds and forces. As the drive shaft 18 may rotate over a wide range of speeds (e.g., at speeds of between zero (0) RPM and 250,000 RPM or higher), the coupling between the drive mechanism and the drive shaft 18 may be configured to withstand such rotational speeds and associated forces.

The drive shaft 18 may be formed from one or more of a variety of materials. For example, the drive shaft 18 may be formed from one or more of a variety of materials, including steel, stainless steel, other metal, polymer, and/or other suitable materials.

The drive shaft 18 may have a suitable diameter and/or length for traversing vasculature of a patient. The diameter and/or the length of the drive shaft 18 may depend on the dimension of the lumen of the elongate member 22, the dimensions of vessels of a patient to be traversed, and/or one or more other suitable factors. In some cases, the drive shaft 18 may have a diameter in a range from about 0.030 centimeters (cm) or smaller to about 0.150 cm or larger and a working length in a range from about ten (10) cm or shorter to about three hundred (300) cm or longer. In one example, the drive shaft 18 may have a diameter of about 0.05715 cm and a length of about fifty (50) cm. Alternatively, the drive shaft 18 may have a different suitable diameter and/or different suitable length.

The atherectomy burr 20 may have an outer perimeter which is equal to or larger than a distal diameter of the drive shaft 18 and/or the elongate member 22. Alternatively or in addition, the atherectomy burr 20 may have an outer perimeter which is smaller than a diameter of the drive shaft 18 and/or the elongate member 22. The atherectomy burr 20 may have a symmetric design so that it penetrates equally well in both rotational directions, but this is not required and the atherectomy burr 20 may be configured to penetrate in only one rotational direction.

The atherectomy burr 20 may be coupled to the drive shaft 18. Where the drive shaft 18 has a first end portion (e.g., a proximal end portion) and a second end portion (e.g., a distal end portion), the atherectomy burr 20 may be coupled to the drive shaft 18 at or near the second end portion. In some cases, the atherectomy burr 20 may be located at or adjacent a terminal end of the second end portion of the drive shaft 18.

The atherectomy burr 20 may be coupled to the drive shaft 18 in any manner. For example, the atherectomy burr 20 may be coupled to the drive shaft 18 with an adhesive connection, a threaded connection, a weld connection, a clamping connection, and/or other suitable connection configured to withstand rotational speeds and forces. Similar to as discussed above with respect to the connection between the drive shaft 18 and the drive mechanism, as the drive shaft 18 and/or the atherectomy burr 20 may rotate at speeds between zero (0) RPM and 250,000 RPM or higher, the coupling between the drive shaft 18 and the atherectomy burr 20 may be configured to withstand such rotational speeds and associated forces.

The drive assembly 12 and the control unit 14 may be in communication and may be located in or may have a same housing and/or located in or have separate housings (e.g., the advancer assembly housing 26 and a control unit housing 28 or other housings). Whether in the same housing or in separate housings, the drive assembly 12 and the control unit 14 may be in communication through a wired connection (e.g., via one or more wires in an electrical connector 24 or other suitable electrical connector) and/or a wireless connection. Wireless connections may be made via one or more communication protocols including, but not limited to, cellular communication, ZigBee, Bluetooth, Wi-Fi, Infrared Data Association (IrDA), dedicated short range communication (DSRC), EnOcean, and/or any other suitable common or proprietary wireless protocol, as desired.

Although not necessarily shown in FIG. 1, the drive assembly 12 may include and/or enclose one or more operational features. For example, among other features, the drive assembly 12 may include a motor (e.g., as discussed above and/or other suitable motor), rubber feet, control electronics, drive circuitry, etc.

The control unit 14, which may be separate from the drive assembly 12 (e.g., as shown in FIG. 1) or may be included in the drive assembly 12, may include several features. For example, as shown in FIG. 1, the control unit 14 may include a display 30 and a control knob 32 (e.g., a motor speed (e.g., RPM or other speed) adjustment knob or other control knob). Additionally or alternatively, the control unit 14 may include one or more other features for controlling the drive mechanism and/or other features of the drive assembly 12 (e.g., one or more drive mechanism states of the drive mechanism) including, but not limited to, a processor, memory, input/output devices, a speaker, volume control buttons, on/off power supply switch, motor activation switch, a timer, a clock, and/or one or more other features.

In some cases, the control unit 14 may include one or more drive mechanism load output control mechanisms for controlling an operation of the atherectomy system 10. In one example of a drive mechanism load output control mechanism that may be included in the control unit 14, the control unit 14 may include a mechanism configured to set and/or adjust an advancing load output (e.g., a rotational speed) and/or a retracting load output from the drive mechanism. Additionally or alternatively, the control unit 14 may include other control and/or safety mechanism for controlling the operation of the atherectomy system 10 and mitigating risks to patients.

In use, there may be times in which the atherectomy burr 20 may partially or even completely occlude blood flow through a vessel, particularly when the atherectomy burr 20 is abrading into and/or through a calcified occlusion. The atherectomy burr 20 may have a diameter that is in the range of 1.25 millimeters (mm) to 5 mm and a length that is in the range of 4 mm to 8 mm. The atherectomy burr 20 may be considered as being adapted to remove calcified material via abrasion, rather than by cutting. The atherectomy burr 20 may include an abrasive material secured to an outer surface of the atherectomy burr 20. In some cases, the abrasive material may be diamond crystals or other diamond-based material.

In some cases, the atherectomy burr 20 may be adapted to permit blood flow through or past the atherectomy burr 20 in situations in which blood flow would be occluded, absent adaptations made to the atherectomy burr. FIGS. 2 through 8 provide illustrative but non-limiting examples of atherectomy burrs that include adaptations such as blood flow enhancement features that permit blood to flow through or around the atherectomy burr when the atherectomy burr is engaged within a blood vessel.

Figure 2:
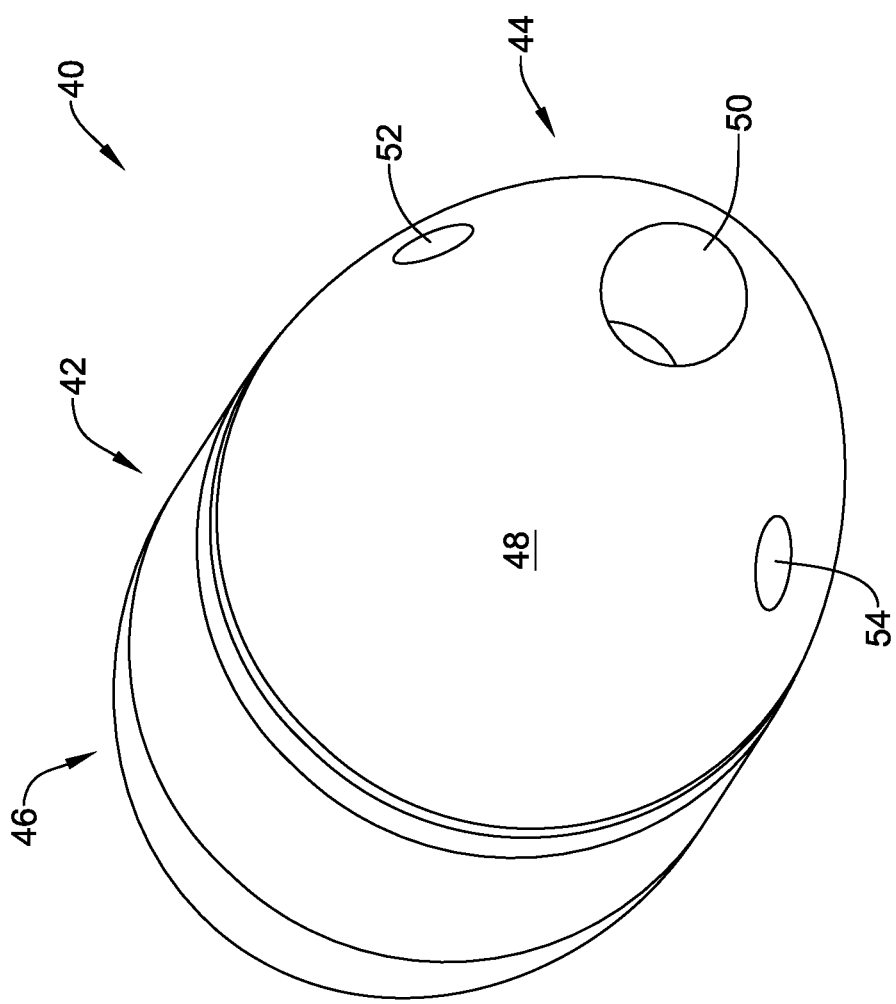
FIG. 2 is a perspective view of an illustrative atherectomy burr usable in the illustrative atherectomy system of FIG. 1.

FIG. 2 is a perspective view of an atherectomy burr 40. The atherectomy burr 40 may be considered as being an example of the atherectomy burr 20 shown in FIG. 1. The atherectomy burr 40 has a burr body 42 that extends from a distal region 44 to a proximal region 46. The burr body 42 includes an outer surface 48 and a lumen 50 that extends through the burr body 42. The atherectomy burr 40 includes blood flow enhancement features that permit blood flow through the atherectomy burr 40 that would not otherwise be feasible. As illustrated, the atherectomy burr 40 includes a first blood flow channel 52 and a second blood flow channel 54. As shown, the first blood flow channel 52 and the second blood flow channel 54 are spaced about 180 degrees apart. In some cases, there may be only one blood flow channel. In some cases, there may be three, four, five, six or more through blood flow channels extending through the burr body 42. It will be appreciated that having more blood flow channels may improve blood flow through the blood flow channels and thus having more blood flow channels may reduce the occlusive impact of the atherectomy burr 40 being in a particular blood vessel, particularly if an overall diameter of the atherectomy burr 40 is close to or equal to a diameter of the particular blood vessel.

The first blood flow channel 52 and the second blood flow channel 54 may each have a cylindrical shape and may exit through the proximal region 46 of the burr body 42. At least one of the first blood flow channel 52 and the second blood flow channel 54, and any additional blood flow channels, if included, may have an ovoid cross-sectional shape. In some instances, the first blood flow channel 52 and the second blood flow channel 54, and any additional blood flow channels, if included, may have a circular cross-sectional shape, a rectilinear cross-sectional shape, a triangular cross-sectional shape, or any other desired cross-sectional shape. The first blood flow channel 52 and/or the second blood flow channel 54 may have a constant internal diameter. In some cases, the first blood flow channel 52 and/or the second blood flow channel 54 may have an internal diameter that increases moving proximally. In some cases, the first blood flow channel 52 and/or the second blood flow channel 54 may have an internal diameter that decreases moving proximally.

In some cases, the first blood flow channel 52 and/or the second blood flow channel 54 may have a circular cross-sectional shape having a diameter in the range of 0.0003 inches to 0.020 inches. In some cases, the first blood flow channel 52 and/or the second blood flow channel 54 may have a circular cross-sectional shape having a diameter that is at least partially dependent on the diameter of the atherectomy burr 40. A larger diameter burr can accommodate a relatively larger diameter blood flow channel, for example, while a smaller diameter burr may be more limited with respect to the size of blood flow channel that can be accommodated. Merely as an illustrative but non-limiting example, an atherectomy burr having a diameter of 1.5 millimeters may have blood flow channels having a diameter of 0.008 inches. An atherectomy burr having a diameter of 2.5 millimeters may have blood flow channels that are proportionally larger. An atherectomy burr having a diameter of 6 millimeters will also have blood flow channels that are proportionally larger.

It will be appreciated that blood cells have an average diameter of about 0.0003 inches, which may be considered as a practical lower limit to the size of the blood flow channels 52 and 54. In some cases, making the blood flow channels 52 and 54 as large as possible can provide increased fluid flow through the atherectomy burr 40, with relatively decreased frictional losses. As the diameter of the blood flow channels 52 and 54 decreases, it will be appreciated that frictional losses caused by boundary layers and other causes can substantially decrease fluid flow through the blood flow channels 52 and 54.

Figure 6:
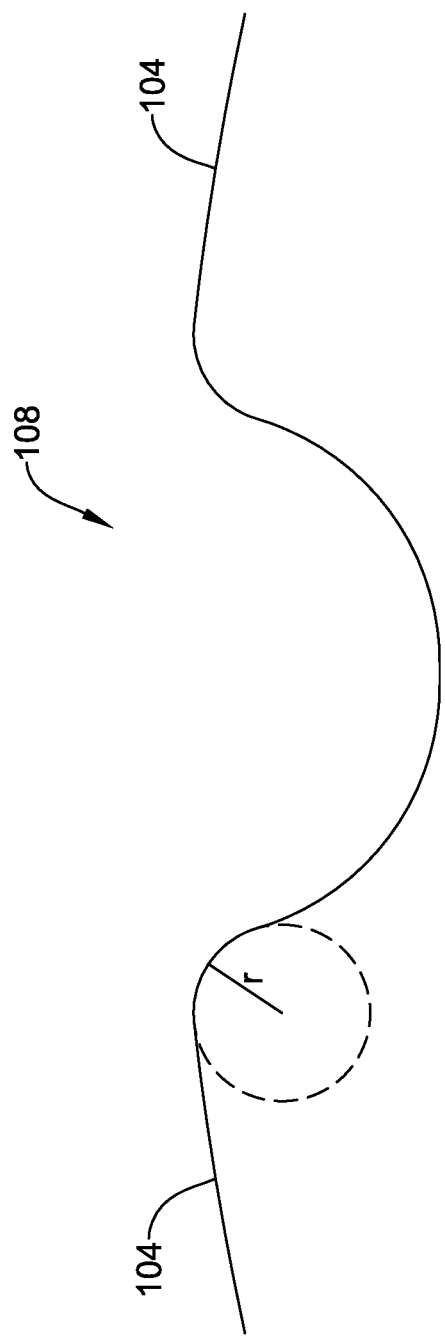
FIG. 6 is an enlarged view of a portion of FIG. 5.

In some cases, the openings to the first blood flow channel 52 and the second blood flow channel 54 may have rounded over edges, such that the edges do not damage blood cells flowing towards and into the first blood flow channel 52 and the second blood flow channel 54. In some cases, the openings to the first blood flow channel 52 and the second blood flow channel 54 may have a radius of curvature that is up to 1 millimeters for smaller diameter atherectomy burrs and a radius of curvature that is up to 10 millimeters for larger diameter burrs. For example, the openings to the first blood flow channel 52 and the second blood flow channel 54 may have a radius of curvature in the range of 0.0001 inches to 0.020 inches. FIG. 6 provides an example defining what the radius of curvature is.

Figure 3:
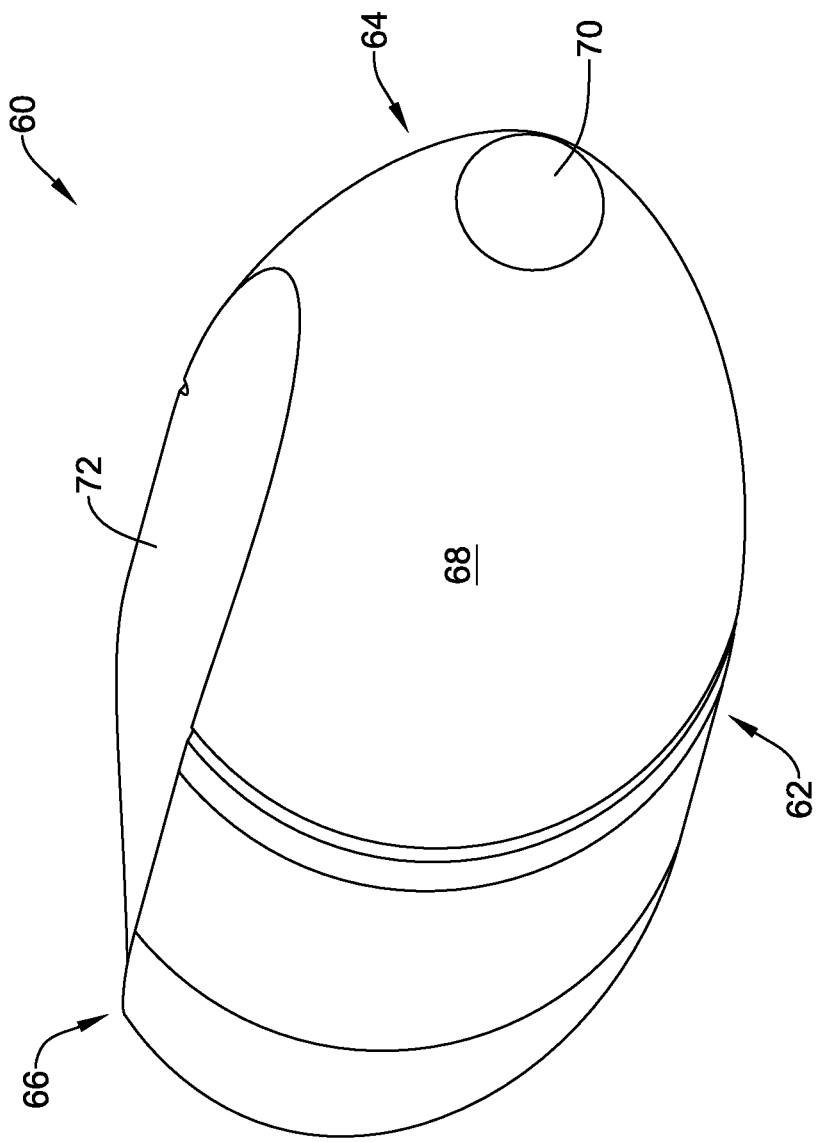
FIG. 3 is a perspective view of an illustrative atherectomy burr usable in the illustrative atherectomy system of FIG. 1.

FIG. 3 is a perspective view of an atherectomy burr 60. The atherectomy burr 60 may be considered as being an example of the atherectomy burr 20 shown in FIG. 1. The atherectomy burr 60 has a burr body 62 that extends from a distal region 64 to a proximal region 66. The burr body 62 includes an outer surface 68 and a lumen 70 that extends through the burr body 62. The atherectomy burr 60 includes blood flow enhancement features that permit blood flow through the atherectomy burr 60 that would not otherwise be feasible. As illustrated, the atherectomy burr 60 includes a single asymmetric cut 72 formed within the outer surface 68. The single asymmetric cut 72 extends from the distal region 64 to the proximal region 66. In some cases, having a single asymmetric cut 72 means that the atherectomy burr 60 is off-balance. As a result, when the atherectomy burr 60 rotates, the atherectomy burr 60 will not simply rotate in place, but will have an orbital path as it rotates. In some cases, this can mean that the atherectomy burr 60 may be able to create a larger hole through an occlusion than would otherwise be possible for a particular size of atherectomy burr 60.

While the asymmetric cut 72 is shown in FIG. 3 as being straight, in some cases the asymmetric cut 72 could instead be spiral-shaped. In some cases, the asymmetric cut 72 may have a length that ranges from 10 percent up to 100 percent of a length of the atherectomy burr 60. A width of the asymmetric cut 72 may be up to 50 percent of a circumference of the atherectomy burr 60, with the circumference measured at a widest point of the atherectomy burr 60. In some cases, the asymmetric cut 72 may have a depth that is up to 50 percent of a diameter of the atherectomy burr 60, with the diameter measured at a widest point of the atherectomy burr 60.

In some instances, the single asymmetric cut 72 has a semi-circular profile. In some cases, the single asymmetric cut 72 may have a flat or linear profile, as would result if one were to simply cut or grind away a portion of the curved burr body 62. The single asymmetric cut 72 may have dimensions of up to 25 percent of the burr diameter. While a single asymmetric cut 72 is illustrated, in some cases the atherectomy burr 60 may include two or more asymmetric cuts 72, spaced unequally around the burr body 62. Depending on how much of an orbital path is desired, the relative spacing between the two or more asymmetric cuts 72 can be varied. If there are two asymmetric cuts 72, for example, and a relatively small orbital path is desired, perhaps the two asymmetric cuts 72 may be spaced 150 to 170 degrees apart (as opposed to 180 degrees, which would be symmetric). If a relatively larger orbital path is desired, the two asymmetric cuts 72 could be spaced 120 degrees part, for example. It will be appreciated that having a larger cut, or having multiple cuts, will improve blood flow past the atherectomy burr 60 but may reduce the available amount of abrasive material. In determining how far apart the asymmetric cuts are spaced, it should be noted that the burr body 62 has a largely cylindrical profile nearer its proximal region 66 and a tapered profile nearer its distal region 64. Spacing may be considered as being defined within the largely cylindrical profile portion of the burr body 62.

In some cases, the edges of the asymmetric cut 72 may be rounded over, such that the edges do not damage blood cells flowing towards and into the asymmetric cut 72. In some cases, the edges of the asymmetric cut 72 may have a radius of curvature that is up to 1 millimeters for smaller diameter atherectomy burrs and a radius of curvature that is up to 10 millimeters for larger diameter burrs. For example, the edges of the asymmetric cut 72 may have a radius of curvature in the range of 0.0001 inches to 0.020 inches. FIG. 6 provides an example defining what the radius of curvature is.

Figure 4:
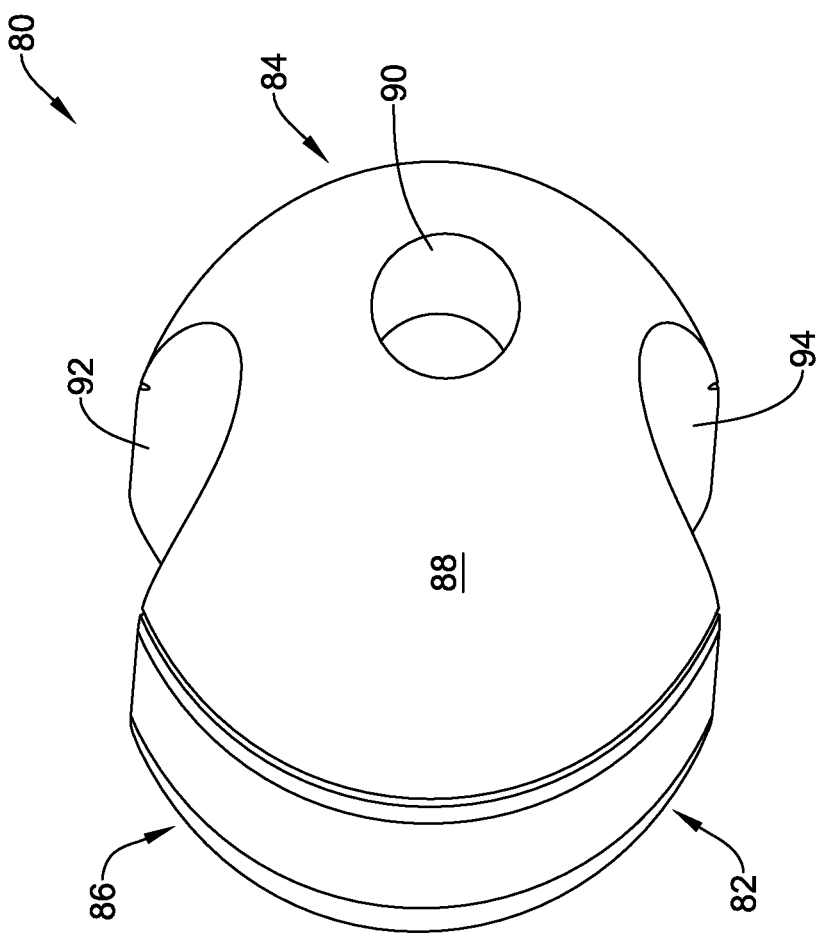
FIG. 4 is a perspective view of an illustrative atherectomy burr usable in the illustrative atherectomy system of FIG. 1.

FIG. 4 is a perspective view of an atherectomy burr 80. The atherectomy burr 80 may be considered as being an example of the atherectomy burr 20 shown in FIG. 1. The atherectomy burr 80 has a burr body 82 that extends from a distal region 84 to a proximal region 86. The burr body 82 includes an outer surface 88 and a lumen 90 that extends through the burr body 82. The atherectomy burr 80 includes blood flow enhancement features that permit blood flow through the atherectomy burr 80 that would not otherwise be feasible. As illustrated, the atherectomy burr 80 includes a first blood flow groove 92 and a second blood flow groove 94. Each of the first blood flow groove 92 and the second blood flow groove 94 extend from the distal region 84 to the proximal region 86 of the burr body 82.

As shown, the first blood flow groove 92 and the second blood flow groove 94 are symmetrically arranged, being spaced 180 degrees apart. As a result, the first blood flow groove 92 and the second blood flow groove 94 will not materially alter the rotational patterns of the atherectomy burr 80. While two blood flow grooves 92, 94 are shown, it will be appreciated that there may be additional blood flow grooves. For example, the atherectomy burr 80 could include a total of three blood flow grooves, each spaced 120 degrees apart. In determining how far apart the blood flow grooves are spaced, it should be noted that the burr body 82 has a largely cylindrical profile nearer its proximal region 86 and a tapered profile nearer its distal region 84. Spacing may be considered as being defined within the largely cylindrical profile portion of the burr body 82. As illustrated, the first blood flow groove 92 and the second blood flow groove 94 each have a semi-circular profile. Each of the first blood flow groove 92 and the second blood flow groove 94 may have dimensions of up to 25 percent of the burr diameter.

In some cases, the edges of the first blood flow groove 92 and the second blood flow groove 94 may be rounded over, such that the edges do not damage blood cells flowing towards and into the first blood flow groove 92 and the second blood flow groove 94. In some cases, the edges of the first blood flow groove 92 and the second blood flow groove 94 may each have a radius of curvature that is up to 1 millimeters for smaller diameter atherectomy burrs and a radius of curvature that is up to 10 millimeters for larger diameter burrs. For example, the edges of the first blood flow groove 92 and the second blood flow groove 94 may have a radius of curvature in the range of 0.0001 inches to 0.020 inches. FIG. 6 provides an example defining what the radius of curvature is.

Figure 5:
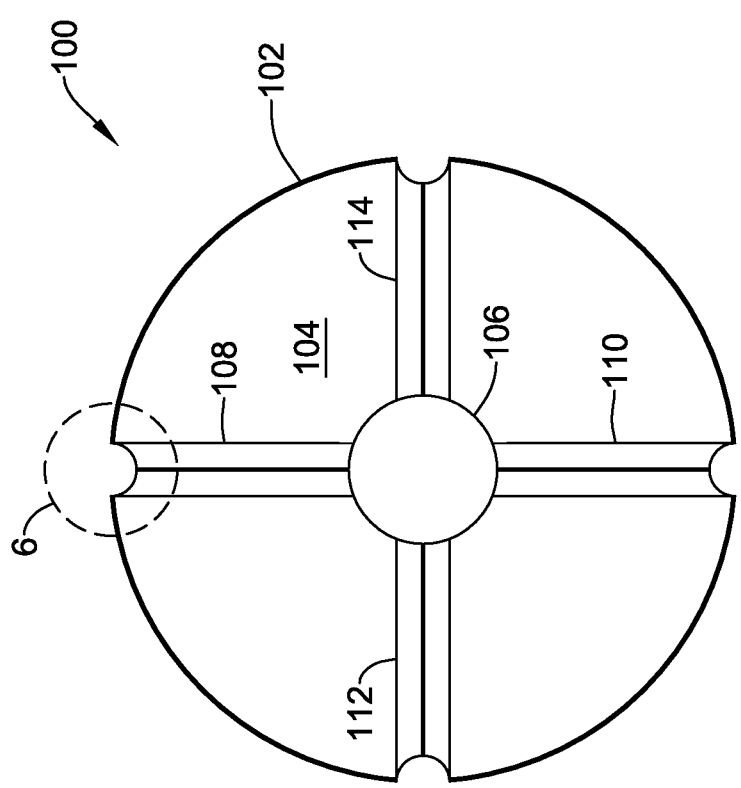
FIG. 5 is an end view of an illustrative atherectomy burr usable in the illustrative atherectomy system of FIG. 1.

FIG. 5 is a perspective view of an atherectomy burr 100. The atherectomy burr 100 may be considered as being an example of the atherectomy burr 20 shown in FIG. 1. The atherectomy burr 100 has a burr body 102 that includes an outer surface 104 and a lumen 106 that extends through the burr body 102. The atherectomy burr 100 includes blood flow enhancement features that permit blood flow through the atherectomy burr 100 that would not otherwise be feasible. As illustrated, the atherectomy burr 100 includes a first blood flow groove 108, a second blood flow groove 110, a third blood flow groove 112 and a fourth blood flow groove 114. The blood flow grooves 108, 110, 112, 114 are equally spaced about the burr body 102 and are 90 degrees apart.

In some cases, there may be additional blood flow grooves formed in the outer surface 104 of the burr body 102. For example, a total of five blood flow grooves could be spaced 72 degrees apart. A total of six blood flow grooves could be spaced 60 degrees apart. These are just examples. As shown, each of the blood flow grooves 108, 110, 112, 114 have a semi-circular profile. In some cases, it is contemplated that one or more of the blood flow grooves 108, 110, 112, 114 could have a V-shaped profile, for example, or a rectilinear profile.

Regardless of the overall shape of the blood flow grooves 108, 110, 112, 114, the edges between each of the blood flow grooves 108, 110, 112, 114 and the outer surface 104 are sufficiently rounded over to prevent the blood flow grooves 108, 110, 112, 114 from serving as cutting edges. FIG. 6 provides an enlarged view of the blood flow groove 108 as illustrative. As can be seen, the transition formed between the blood flow groove 108 and the outer surface 104 has a radius of curvature 'r' that limits or even prevents any part of the blood flow groove 108 from cutting or substantially cutting tissue. As noted, the atherectomy burr 20, and the atherectomy burrs 40, 60, 80, 100 discussed thus far are intended to function as abrasive burrs, not cutting burrs. Accordingly, the transition formed between the blood flow groove 108 and the outer surface 104 has a radius of curvature of up to 10 millimeters for large atherectomy burrs and a radius of curvature of up to 1 millimeters for small atherectomy burrs. As an example, the transition between the blood flow groove 108 and the outer surface 104 may have a radius of curvature in the range of 0.0001 inches to 0.020 inches.

Figure 7:
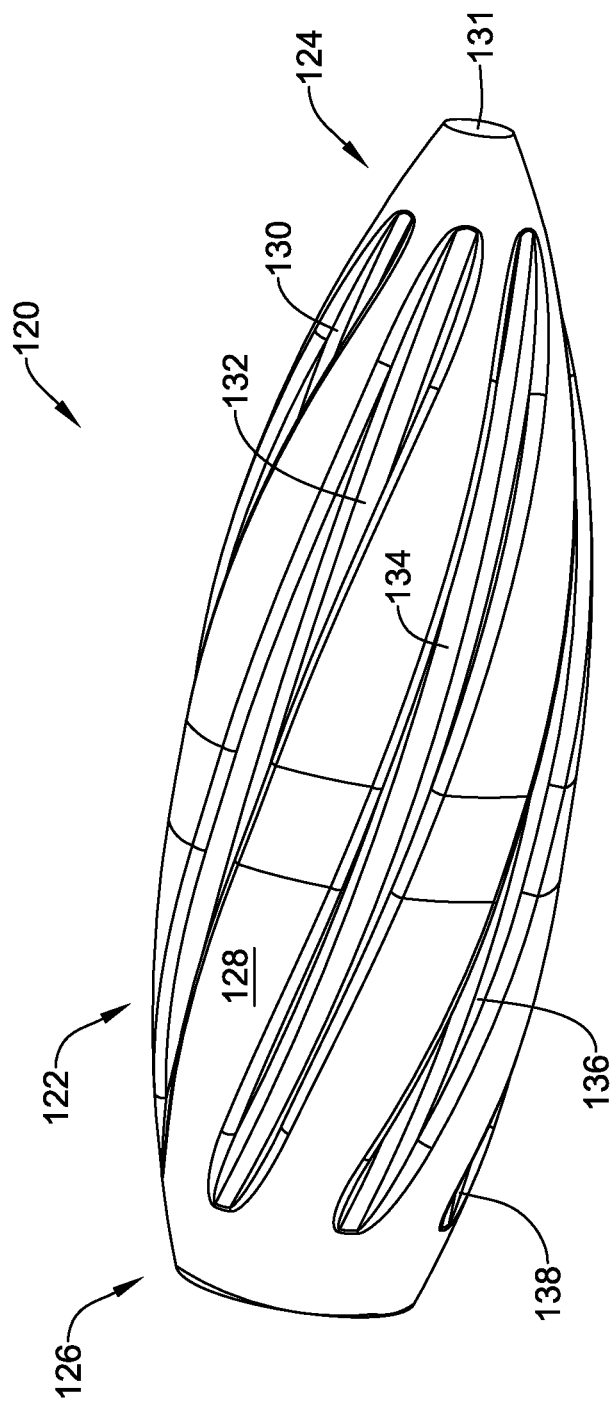
FIG. 7 is a perspective view of an illustrative atherectomy burr usable in the illustrative atherectomy system of FIG. 1.

FIG. 7 is a perspective view of an atherectomy burr 120. The atherectomy burr 120 may be considered as being an example of the atherectomy burr 20 shown in FIG. 1. The atherectomy burr 120 has a burr body 122 that extends from a distal region 124 to a proximal region 126. The burr body 122 includes an outer surface 128 and a lumen 131 that extends through the burr body 122. The atherectomy burr 120 includes blood flow enhancement features that permit blood flow through the atherectomy burr 120 that would not otherwise be feasible. As illustrated, the atherectomy burr 120 includes a number of fluted cuts, including fluted cuts 130, 132, 134, 136 and 138 that are visible in this illustration.

In some cases, the atherectomy burr 120 may include from two (2) to fifteen (14) fluted cuts. The atherectomy burr 120 may include from four (4) to ten (10) fluted cuts. The atherectomy burr 120 may include from six (6) to eight (8) fluted cuts. In some cases, the atherectomy burr 120 may include a total of six (6) or eight (8) fluted cuts. Each of the fluted cuts 130, 132, 134, 136 and 138 may have a length that ranges from ten (10) percent to one hundred (100) percent of a length of the atherectomy burr 120. Each of the fluted cuts 130, 132, 134, 136 and 138 may have a depth that ranges from near zero (0) to twenty five (25) percent of a diameter of the atherectomy burr 120. In the case of a six (6) millimeter diameter atherectomy burr, the depth may be as great as forty (40) percent of the diameter. Each of the fluted cuts 130, 132, 134, 136 and 138 may have a width that is up to fifty (50) percent of a diameter of the atherectomy burr 120, with a caveat that a combined width (adding the width of each of the fluted cuts) does not exceed ninety (90) or ninety five (95) percent of the diameter of the atherectomy burr 120.

Figure 8:
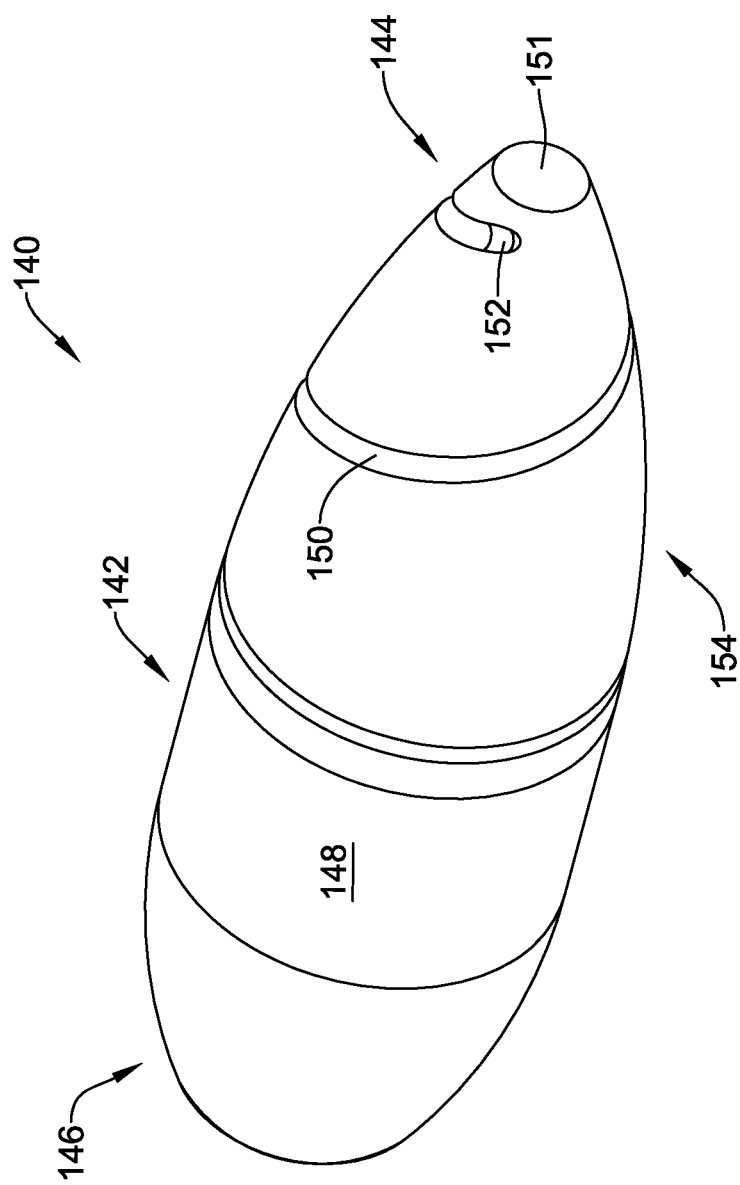
FIG. 8 is a perspective view of an illustrative atherectomy burr usable in the illustrative atherectomy system of FIG. 1.

FIG. 8 is a perspective view of an atherectomy burr 140. The atherectomy burr 140 may be considered as being an example of the atherectomy burr 20 shown in FIG. 1. The atherectomy burr 140 has a burr body 142 that extends from a distal region 144 to a proximal region 146. The burr body 142 includes an outer surface 148 and a lumen 151 that extends through the burr body 142. The atherectomy burr 140 includes blood flow enhancement features that permit blood flow through the atherectomy burr 140 that would not otherwise be feasible. As illustrated, the atherectomy burr 140 includes a spiral blood flow groove 150 that extends from a distal end 152 that is disposed within the distal region 144 to a proximal end 154 (not visible). In some cases, the spiral blood flow groove 150 may have a depth that is up to forty (40) or forty five (45) percent of a diameter of the atherectomy burr 140. The spiral blood flow groove 150 has a rounded-over transition between the spiral blood flow groove 150 and the outer surface 148 such that the spiral blood flow groove 150 does not form any cutting edges, similar to that discussed with respect to FIG. 6.

Figure 9:
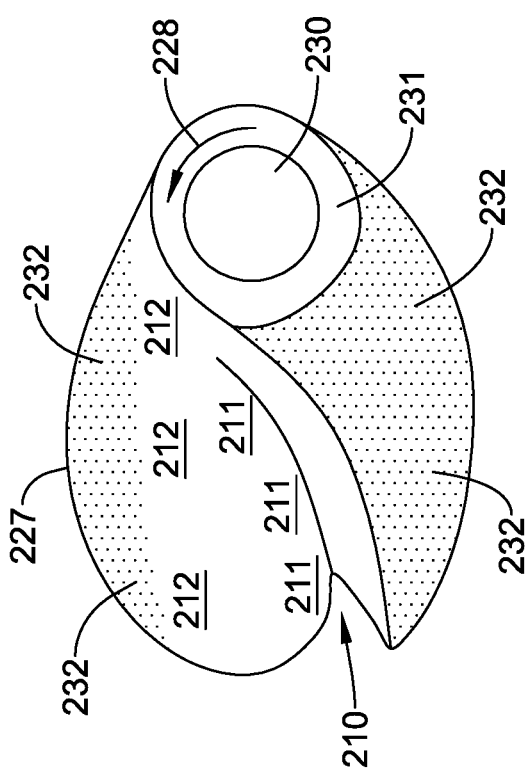
FIG. 9 is a perspective view of an illustrative atherectomy burr usable in the illustrative atherectomy system of FIG. 1.

FIG. 9 is a perspective view of an illustrative atherectomy burr 227 having a guidewire entry port 230 that is surrounded by a buffer zone 231 located at the front. The buffer zone 231 may be free of abrasive material. The atherectomy burr 227 includes a semi-spiral channel 210 having a low pitch, where pitch is defined as number of degrees of twist per centimeter of length. The semi-spiral channel 210 may serve to pump blood as the atherectomy burr 227 rotates in a direction indicated by an arrow 228. In some cases, the semi-spiral channel 231 pushes blood and debris distally, in a manner similar to that of a marine propeller. It will be appreciated that each element of the blood volume may receive a vector component of force in the distal direction.

The semi-spiral channel 210 may have a leading edge 211 that is substantially rounded or chamfered over a distance that ranges from 0.02 to 10 times a width of the blood flow channel, or a distance that ranges from 0.05 to 10 times the width of the blood flow channel provided by the semi-spiral channel 210. As a result, not only does the leading edge 211 not provide a cutting feature, but the leading edge 211 also provides for a gradual return of rebounded tissue residing in the semi-spiral channel 210 to a surface 212 that is equal to the burr maximum at each position in the longitudinal direction. Furthermore, the tissue is not engaged by diamond crystals 232 until it has stabilized in an orbit equal to the burr's maximum radius of gyration. As a result, healthy compliant tissue will not be engaged by the diamond crystals 232 beyond its elastic limit, thereby preserving differential cutting. Differential cutting refers to a process whereby diseased tissue having inelastic properties is differentially removed while healthy tissue, which is elastic, is spared.

Figure 10:
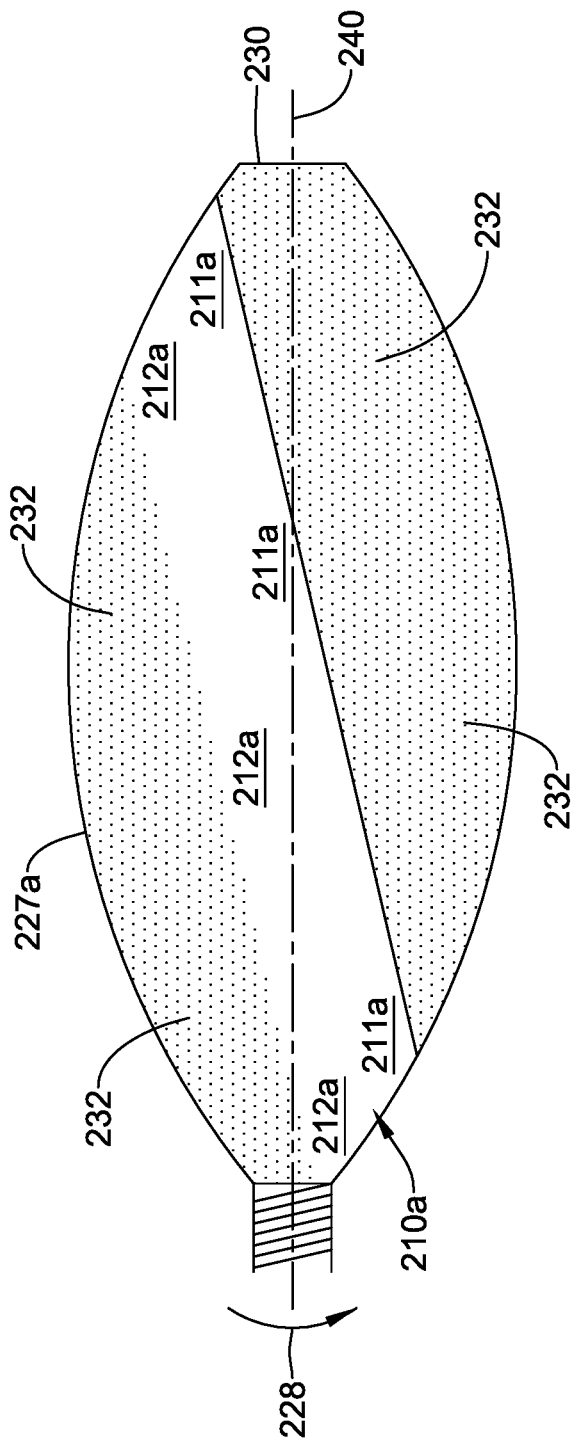
FIG. 10 is a perspective view of an illustrative atherectomy burr usable in the illustrative atherectomy system of FIG. 1.

FIG. 10 is a side view of an illustrative atherectomy burr 227a having a guidewire entry port 230 that is surrounded by a buffer zone 231 located at the front. The buffer zone 231 may be free of abrasive material. The atherectomy burr 227a includes a channel 210a that is straight, but at a small angle with respect to a longitudinal axis 240. With rotation in the direction indicated by the arrow 228, blood will be pushed in the distal direction by the channel 210a. As in FIG. 9, the leading edge 211a is substantially rounded or chamfered over a distance that ranges from 0.02 to 10 times a width of the blood flow channel provided by the channel 210a, or a distance that ranges from 0.05 to 10 times the width of the blood flow channel. As a result, the leading edge 211a does not provide a cutting feature, but the leading edge 211a does provide for a gradual return of rebounded tissue residing in the channel 210a to a surface 212a that is equal to the burr maximum at each position in the longitudinal direction. Furthermore, the tissue is not engaged by diamond crystals 232 until it has stabilized in an orbit equal to the burr's maximum radius of gyration. As a result, healthy compliant tissue will not be engaged by the diamond crystals 232 beyond its elastic limit, thereby preserving differential cutting. Differential cutting refers to a process whereby diseased tissue having inelastic properties is differentially removed while healthy tissue, which is elastic, is spared.

Experimental Section

Several burr designs were tested to see how the particular designs affected fluid flow past the burr. The tested designs are designated in the data below as Fluted (corresponding to FIG. 7), Scallop (corresponding to FIG. 3) and Through Hole (corresponding to FIG. 2). A production burr lacking any blow flow enhancement features was included as a control.

To perform the testing, burr blanks were loaded onto a production equivalent 0.009 section of ROTAWIRE DRIVE and this subassembly was loaded into a clear HDPE tube with a 1.75 mm ID in a near straight configuration. The tube had a slight memory from being on spool and was flooded with red food coloring dyed DI water. Tubing was placed into a 6F compatible Hemostasis valve with Y-luer adapter port such that the proximal end of the tubing was just distal to the point in the hemostasis valve where the 'y' connects. The entry point on the hemostasis valve was closed and the 'y' port was connected to a 1 L bag of DI water and food coloring that was pressurized to 200±25 mmHg via pressure cuff, which was monitored and repressured at the start and during each test. The distal end of the tube was place over a collection beaker that had been wet weighed with the DI/food coloring mix. The pressurized bag was open as a timer was started. The burrs were not separately driven into rotation during testing.

Figure 11:
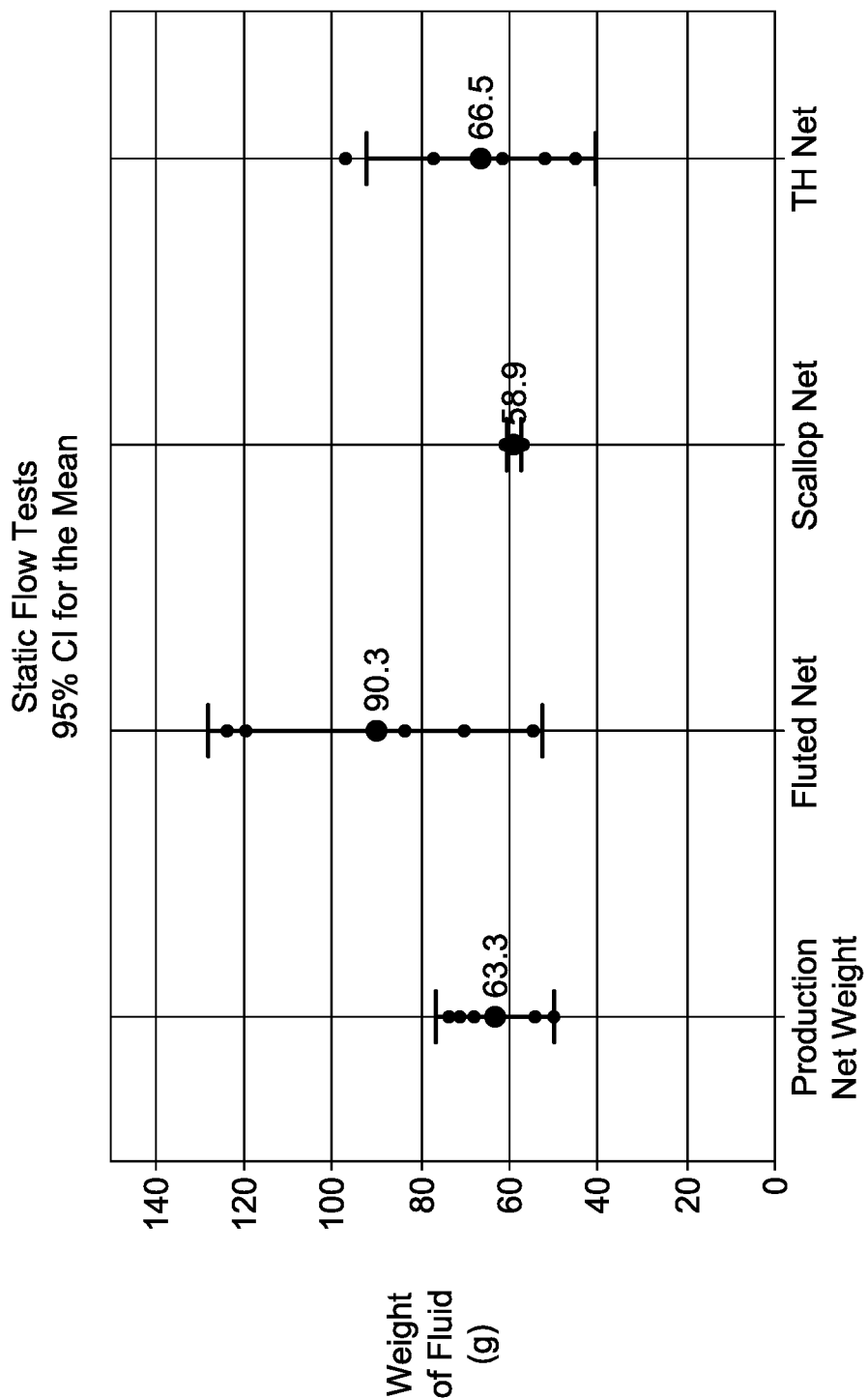
FIG. 11 is a graph illustrating experimental data.

Fluid was collected in a beaker for roughly 30 seconds (within a margin of error for a human to close the IV line connecting the bag to the hemostasis valve. The fluid was weighed using a scale calibrated to ±0.5 g by weighing the beaker plus fluid and subtracting the weight of the empty beaker, where the empty beaker weighed 14.5 grams (g). Because water has a density of 1 g/ml, the net mass flow amounts listed below can also be considered as volumes, measured in milliliters (ml). The experimental data is shown below in Table One. The net mass data is graphically represented in FIG. 11.

TABLE ONE

| Run # | Control | | Fluted | | Scallop | | Through Hole | |
|---|---|---|---|---|---|---|---|---|
| | Gross Weight (g) | Net Weight (g) | Gross Weight (g) | Net Weight Net (g) | Gross Weight (g) | Net Weight (g) | Gross Weight (g) | Net Weight (g) |
| 1 | 64 | 49.5 | 84.5 | 70 | 75 | 60.5 | 59.5 | 45 |
| 2 | 68.5 | 54 | 98 | 83.5 | 73 | 58.5 | 76 | 61.5 |
| 3 | 86 | 74.5 | 134 | 119.5 | 74 | 59.5 | 66.5 | 52 |
| 4 | 82.5 | 68 | 138.5 | 124 | 71.5 | 57 | 111.5 | 97 |
| 5 | 88 | 73.5 | 69 | 54.5 | 73.5 | 59 | 91.5 | 77 |

Several observations were made during testing. There was considerable variation between runs for the Fluted burr. For the runs with a higher flow amount (runs 2, 3 and 4), the flow of fluid through the tube caused the Fluted burr to begin rotating. The Fluted burr rotated at an estimated rotation speed of 5 to 10 revolutions per second. As the Fluted burr rotated, the design of the Fluted burr caused a pumping effect, further increasing fluid flow past the burr. For the runs with a lower flow amount (runs 1 and 5), the Fluted burr did not spin, as apparently there was sufficient friction between the Fluted burr and the side of the tubing (due to a small curve in the tubing) that prevented rotation.

With respect to the Scallop burr, regardless of how the Scallop burr was originally oriented within the tubing, as soon as flow began, the burr seemed to rotate to be on the inside of the slight curve in the tubing. This may have impacted the flow results for the Scallop burr.

For the Through Hole burr, an air pocket seems to have formed when pre-flooding the tube prior to collecting fluid. One possibility is that the fluid goes around the outside of the burr first, which doesn't allow any air trapped within the through holes to escape.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy burr adapted for use in a rotational atherectomy system, the atherectomy burr comprising:
   an atherectomy burr body extending from a distal region to a proximal region thereof, the proximal region adapted to be secured relative to a drive cable of a rotational atherectomy system;
   the atherectomy burr body defining an outer surface; and
   one or more blood flow enhancement features adapted to increase blood flow past the burr;
   the one or more blood flow enhancement features including an asymmetric flow channel formed within the outer surface of the atherectomy burr, where the asymmetric flow channel includes a chamfered leading edge adapted to not abrade tissue, an outer surface rotationally before the asymmetric flow channel that includes abrasive material for abrading tissue, and an outer surface rotationally beyond the asymmetric flow channel that is free of abrasive material in order to allow rebounded tissue to stabilize before contacting abrasive material outside of the surface;
   wherein the one or more flow enhancement features are adapted to provide preferential cutting of inelastic material relative to elastic material.

2. The atherectomy burr of claim 1, wherein the asymmetric flow channel comprises a single asymmetric cut within the burr body.

3. The atherectomy burr of claim 1, wherein the one or more blood flow enhancement features further comprise a plurality of symmetrically arranged blood flow grooves extending axially along a length of the burr body.

4. The atherectomy burr of claim 1, wherein the one or more blood flow enhancement features further comprise two or more blood flow channels that are asymmetrically arranged about the outer surface of the atherectomy burr.

5. The atherectomy burr of claim 1, wherein the flow channel comprises a semi-spiral channel.

6. The atherectomy burr of claim 1, wherein the flow channel further comprises a straight flow channel arranged at an angle with respect to a longitudinal axis of the atherectomy burr.

* * * * *